United States Patent
Chiba et al.

(10) Patent No.: US 7,193,108 B2
(45) Date of Patent: Mar. 20, 2007

(54) PHENYLPROPIONIC ACID DERIVATIVES

(75) Inventors: Akira Chiba, Kawasaki (JP);
Kazuyuki Sagi, Kawasaki (JP);
Toshihiko Yoshimura, Kawasaki (JP);
Tatsuya Okuzumi, Kawasaki (JP);
Hiroyuki Izawa, Kawasaki (JP);
Masahiro Murata, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 619 days.

(21) Appl. No.: 10/763,237

(22) Filed: Jan. 26, 2004

(65) Prior Publication Data

US 2004/0236147 A1    Nov. 25, 2004

Related U.S. Application Data

(63) Continuation of application No. PCT/JP02/07543, filed on Jul. 25, 2002.

(30) Foreign Application Priority Data

Jul. 26, 2001 (JP) ............................ 2001-225749

(51) Int. Cl.
*C07C 315/00* (2006.01)
*C07C 317/00* (2006.01)
*C07C 229/00* (2006.01)
*A61K 31/00* (2006.01)

(52) U.S. Cl. ...................... 562/430; 562/450; 514/183; 514/506; 514/554; 514/580; 514/613

(58) Field of Classification Search .................... None
See application file for complete search history.

(56) References Cited

U.S. PATENT DOCUMENTS

2003/0149083 A1    8/2003    Tanaka et al. .............. 514/357
2003/0220268 A1    11/2003   Makino et al. ............... 514/19

FOREIGN PATENT DOCUMENTS

| JP | 10-509146   | 9/1998 |
| WO | WO 96/15096 | 5/1996 |
| WO | WO 99/10313 | 3/1999 |
| WO | WO 99/36393 | 7/1999 |
| WO | WO 00/05223 | 2/2000 |

OTHER PUBLICATIONS

U.S. Appl. No. 10/866,260, filed Jun. 14, 2004, Okuzumi et al.
U.S. Appl. No. 10/921,929, filed Aug. 20, 2004, Sagi et al.

*Primary Examiner*—Sikarl A. Witherspoon
(74) *Attorney, Agent, or Firm*—Oblon, Spivak, McClelland, Maier & Neustadt, P.C.

(57) ABSTRACT

Specified phenylpropionic acid derivatives and analogues thereof have an antagonistic activity to α 4 integrin. They are used as therapeutic agents or preventive agents for various diseases concerning α 4 integrin, such as inflammatory diseases in which α 4 integrin-depending adhesion process participates in the pathology, rheumatoid arthritis, inflammatory bowel diseases, systemic lupus erythematosus, multiple sclerosis, Sjögren's syndrome, asthma, psoriasis, allergy, diabetes, cardiovascular diseases, arterial sclerosis, restenosis, tumor proliferation, tumor metastasis and transplantation rejection.

24 Claims, No Drawings

PHENYLPROPIONIC ACID DERIVATIVES

CROSS-REFERENCE TO RELATED APPLICATIONS

This application is a continuation of International Application No. PCT/JP02/07543, which was filed on Jul. 25, 2002, which claims priority to Japanese application JP 2001-225749, filed on Jul. 26, 2001. The entire contents of both applications are incorporated herein by references.

BACKGROUND OF THE INVENTION

The present invention relates to new phenylpropionic acid derivatives and the use of the phenylpropionic acid derivatives as medicines. The present invention also relates to the compounds usable as therapeutic agents or preventive agents for inflammatory diseases in which α 4 integrin-depending adhesion process participates in the pathology. It was reported that α 4 integrins participate in rheumatoid arthritis, inflammatory bowel diseases, systemic lupus erythematosus, multiple sclerosis, Sjögren's syndrome, asthma, psoriasis, allergy, diabetes, cardiovascular diseases, arterial sclerosis, restenosis, tumor proliferation, tumor metastasis and transplantation rejection. The compounds of the present invention having an antagonistic effect on the α 4 integrins are usable as therapeutic agents or preventive agents for the above-described diseases.

In the inflammatory reactions, it is generally understood that when a microorganism invades a tissue or when the tissue is injured, leukocytes play an important role for the exclusion of the microorganism or for the repair of the injured tissue. It is also widely understood that in such cases, leukocytes usually circulating in the blood must pass through the vascular wall and be newly supplied to the injured tissue. It has been elucidated that the infiltration of the leukocytes from the blood vessel into the tissue is carried out by integrin molecules which are a group of heterodimeric proteins expressing on the leukocytes. The integrin molecules are classified into at least 8 subfamilies (β 1 through β 8 subfamilies) depending on the β chains thereof. Known typical subfamilies are β 1 and β 3 subfamilies involved in the adhesion of cell ingredients to the extracellular matrix such as collagen and fibronectin; β 2 subfamily involved in cell-to-cell adhesion in the immune system; and β 7 subfamily which mainly participates in the infiltration of leukocytes into mucosal tissues (Shimizu et al., Adv. Immunol. 72: 325–380, 1999). As for the above-described α 4 integrins, two kinds of molecules thereof are known. They are VLA-4 (very late antigen-4) molecule belonging to the β 1 subfamily and comprising α 4 β 1 chain and LPAM-1 (lymphocyte Peyer's patch HEV adhesion molecule-1) molecule belonging to the β 7 subfamily and comprising α 4 β 7 chain. Usually most of leukocytes circulating in the blood have only a low adhesion affinity for the vascular-endothelium cells and they cannot move out of the blood vessel. However, lymphocytes mainly comprising T cells and B cells are capable of moving out of the blood vessel by a so-called lymphocyte homing phenomenon wherein they move from the blood into the lymphoid tissue through the blood vessel wall and then they return into the blood through the lymphatic vessel under the physiological conditions. It is known that LPAM-1 molecules participate in the lymphocyte homing into the lymphoid tissue of an intestinal tract such as Peyer's patch (Butcher et al., Adv. Immunol. 72: 209–253, 1999). On the other hand, when an inflammation occurs, the vascular-endothelium cells are activated by cytokine and chemokine released from the inflamed tissue, the expression of a group of cell surface antigens (adhesion molecules) participating in the adhesion of leukocytes to the vascular-endothelium cells is caused, and a lot of leukocytes infiltrate out of the blood vessel toward the inflamed tissue through the adhesion molecules.

As the cell surface antigens on the vascular-endothelium cells participating in the adhesion of the leukocytes, there have been known E-selectin (adhesion molecule mainly participating in the adhesion of neutrophils), ICAM-1 and VCAM-1 mainly participating in the adhesion of lymphocytes, and MAdCAM-1 mainly participating in the adhesion of lymphocytes in the lymphoid tissue of an intestinal tract such as Peyer's patch (Shimizu et al., Adv. Immunol. 72: 325–380, 1999). It was reported that in those adhesion molecules, VCAM-1 acts as a ligand of both VLA-4 and LPAM-1 and that MAdCAM-1 acts as the ligand of LPAM-1. As a ligand of both VLA-4 and LPAM-1, fibronectin which is a kind of extracellular matrix is also known (Shimizu et al., Adv. Immunol. 72: 325–380, 1999). The β 1 integrin subfamily to which VLA-4 belongs comprises at least 6 integrins (VLA-1 to VLA-6) using extracellular matrixes such as fibronectin, collagen and laminin as the ligands. Many of integrins using extracellular matrixes as the ligands, such as VLA-5, β 3 subfamily and β 5 subfamily, recognize arginine-glycine-aspartic acid (RGD) sequence in fibronectin, vitronectin, tenascin and osteopontin. On the other hand, in the interaction of VLA-4 and fibronectin, the RGD sequence does not participate but a CS-1 peptide segment comprising leucine-aspartic acid-valine (LDV) as the core sequence participates (Pulido et al., J. Biol. Chem. 266: 10241–10245, 1991). Clements et al. found a sequence similar to LDV in amino acid sequences of VCAM-1 and MAdCAM-1. It has been elucidated that a variant obtained by partially modifying the CS-1-like sequence of VCAM-1 and MAdCAM-1 molecules cannot interact to VLA-4 or LPAM-1 (Clements et al., J. Cell Sci. 107: 2127–2135, 1994, Vonderheide et al., J. Cell. Biol. 125: 215–222, 1994, Renz et al., J. Cell. Biol. 125: 1395–1406, 1994, and Kilger et al., Int. Immunol. 9: 219–226, 1997). Thus, it was found that the CS-1-like sequence is important for the interaction of VLA-4/LPAM-1 and VCAM-1/MAdCAM-1.

It was also reported that the cyclic peptide having the CS-1-like structure is antagonistic both to the interaction of VLA-4 or LPAM-1 with VCAM-1, MAdCAM-1 or CS-1 peptide (Vanderslice et al., J. Immunol. 158: 1710–1718, 1997). The above-described facts indicate that all the interactions of α 4 integrin and VCAM-1, MAdCAM-1 or fibronectin can be blocked by using a suitable α 4 integrin antagonist (the term "α 4 integrin antagonist" in the specification indicates a substance antagonistic to α 4 β 1 and/or α 4 β 7 integrin).

It is also known that the expression of VCAM-1 in vascular-endothelium cells is caused by inflammatory factors such as LPS, TNF-α or IL-1 and that when the inflammation occurs, the infiltration of the leukocytes from the blood vessel into the tissue is carried out by the VLA-4/VCAM-1 adhesion mechanism (Elices, Cell 60: 577–584, 1990, Osborn et al., Cell 59: 1203–1211, 1989 and Issekutz et al., J. Eex. Med. 183: 2175–2184, 1996). Because VLA-4 is expressed on the surfaces of activated lymphocytes, monocytes, eosinophils, mast cells and neutrophils, the adhesion mechanism of VLA-4/VCAM-1 plays an important role for the infiltration of those cells into the inflamed tissue. It was reported that VLA-4 is expressed on various sarcoma cells such as melanoma cells, and it was also elucidated that the adhesion mechanism of VLA-4/VCAM-1 participates in the metastasis of these tumors. By investigating the expression of VCAM-1 in various pathological tissues, it was made apparent that the adhesion mechanism of this VLA-4/VCAM-1 participates in various pathological stages. Namely, it was reported that in addition to the activated vascular-endothelium cells, the expression of VCAM-1 is increased in the inflamed tissues in the patients with autoimmune diseases such as rheumatoid synovial membrane (van Dinther-Janssen, J. Immunol. 147: 4207–4210, 1991 and Morales-Ducret et al., J. Immunol. 149: 1424–1431, 1992), lungs and respiratory tract epithelium in asthma (ten Hacken et al., Clin. Exp. Allergy 12: 1518–1525, 1998) and allergic diseases (Randolph et al., J. Clin. Invest. 104: 1021–1029, 1999), systemic lupus erythematosus (Takeuchi et al., J. Clin. Invest. 92: 3008–3016, 1993), Sjögren's syndrome (Edwards et al., Ann. Rheum. Dis. 52: 806–811, 1993), multiple sclerosis (Steffen et al., Am. J. Pathol. 145: 189–201, 1994) and psoriasis (Groves et al., J. Am. Acad. Dermatol. 29: 67–72, 1993); atherosclerotic plagues (O'Brien et al., J. Clin. Invest. 92: 945–951, 1993), intestinal tissues of the patients with inflammatory bowel diseases such as Crohn's disease and ulcerative colitis (Koizumi et al., Gastroenterol. 103: 840–847, 1992 and Nakamura et al., Lab. Invest. 69: 77–85, 1993), inflamed tissue of Langerhans island of patients with diabetes (Martin et al., J. Autoimmun. 9: 637–643, 1996) and implants during the rejection of transplantation of heart or kidney (Herskowitz et al. Am. J. Pathol. 145: 1082–1094, 1994 and Hill et al., Kidney Int. 47: 1383–1391, 1995). The adhesion mechanism of VLA-4/VCAM-1 participates in these various diseases.

There are many reports showing that in vivo administration of VLA-4 or VCAM-1 antibody was effective in improving the diseases of animal models with those inflammatory diseases. Concretely, Yednock et al. and Baron et al. reported that the in vivo administration of an antibody against α 4 integrins was effective in controlling the incidence rate or in controlling encephalomyelitis in the experimental autoimmune encephalomyelitis models, i.e. multiple sclerosis models (Yednock et al., Nature 356: 63–66, 1992 and Baron et al., J. Exp. Med. 177: 57–68, 1993). Zeidler et al. reported that in vivo administration of an antibody against α 4-integrin was effective in controlling the incidence rate of mouse collagen arthritis (rheumatoid models) (Zeidler et al., Autoimmunity 21: 245–252, 1995). The therapeutic effect of an antibody against α 4-integrin in asthma models was reported by Abraham et al. and Sagara et al. (Abraham et al., J. Clin. Invest. 93: 776–787, 1994 and Sagara et al., Int. Arch. Allergy Immunol. 112: 287–294, 1997). The effect of an antibody against α 4-integrin in inflammatory bowel disease models was reported by Podolsky et al. (Podolsky et al., J. Clin. Invest. 92: 372–380, 1993). The effect of an antibody against α 4-integrin and that against VCAM antibody in insulin-dependent diabetes models were reported by Baron et al. (Baron et al., J. Clin. Invest. 93: 1700–1708, 1994). It was made apparent with baboon models that the restenosis of a blood vessel after an angioplasty carried out because of arteriosclerosis can be inhibited by the administration of α 4 integrin antibody (Lumsden et al., J. Vasc. Surg. 26: 87–93, 1997). It was also reported that α 4 integrin or VCAM antibody is effective in inhibiting the rejection of an implant or inhibiting metastasis of a cancer (Isobe et al., J. Immunol. 153: 5810–5818, 1994 and Okahara et al., Cancer Res. 54: 3233–3236, 1994).

As described above, unlike VCAM-1, MAdCAM-1 which is a ligand of LPAM-1 is constitutively expressed on high endothelial venules (HEV) in the intestinal mucosa, mesenteric lymphatic nodes, Peyer's patch and spleen and it participates in the homing of mucosal lymphocytes. It is also known that LPAM-1/MAdCAM-1 adhesion mechanism not only has physiological roles in the homing of the lymphocytes but also participates in some pathological processes. Briskin et al reported an increase in the expression of MAdCAM-1 in inflamed regions in intestinal tracts of patients with inflammatory bowel diseases such as Crohn's disease and ulcerative colitis (Briskin et al., Am. J. Pathol. 151: 97–110, 1997). Hanninen et al. reported that induction of the expression is observed in an inflamed tissue of Langerhans island of NOD mouse which is a model of an insulin-dependent diabetes (Hanninen et al., J. Immunol. 160: 6018–6025, 1998). The fact that LPAM-1/MAdCAM-1 adhesion mechanism participates in the progress of diseases is apparent from the fact that conditions of mouse models with inflammatory bowel disease (Picarella et al., J. Immunol. 158: 2099–2106, 1997) and the above-described NOD mouse models are improved by the in vivo administration of antibody to MAdCAM or antibody to β 7 integrin (Hanninen et al., J. Immunol. 160: 6018–6025, 1998 and Yang et al., Diabetes 46: 1542–1547, 1997).

The above-described facts indicate the possibility in that employing the blocking of VLA-4/VCAM-1, LPAM-1/VCAM-1 or LPAM-1/MAdCAM-1 adhesion mechanism by a suitable antagonist is effective in treating the chronic inflammatory diseases described above. The use of the antibody against VLA-4 as the VLA-4 antagonist is described in WO 93/13798, WO 93/15764, WO 94/16094 and WO 95/19790. Peptide compounds as VLA-4 antagonists are described in WO 94/15958, WO 95/15973, WO 96/00581 and WO 96/06108. Amino acid derivatives usable as VLA-4 antagonists are described in WO 99/10313 and WO 99/36393. However, none of them is practically used for the therapeutic treatment at present because of the lack of oral bioavailability and immunogenic properties during the use of them for a long period of time.

DISCLOSURE OF THE INVENTION

An object of the present invention is to provide new compounds having α 4 integrin antagonistic effect.

Another object of the present invention is to provide a pharmaceutical composition containing such a new compound(s).

Still another object of the present invention is to provide α 4 integrin antagonists.

An additional object of the present invention is to provide therapeutic agents or preventive agents for diseases in which α 4 integrin-depending adhesion process participates in the pathology, such as inflammatory diseases, rheumatoid arthritis, inflammatory bowel diseases, systemic lupus erythematosus, multiple sclerosis, Sjögren's syndrome, asthma, psoriasis, allergy, diabetes, cardiovascular diseases, arterial sclerosis, restenosis, tumor proliferation, tumor metastasis and transplantation rejection.

For the purpose of solving the above-described problems, the inventors have synthesized various phenylpropionic acid derivatives and examined α 4 integrin antagonistic activities thereof, and the inventors have found that specified, new phenylpropionic acid derivatives, especially the compounds of the following general formula (1), have an excellent α 4 integrin antagonistic activity. The present invention has been completed on the basis of this finding.

Namely, the present invention provides phenylpropionic acid derivatives of the following general formula (1) or pharmaceutically acceptable salts thereof:

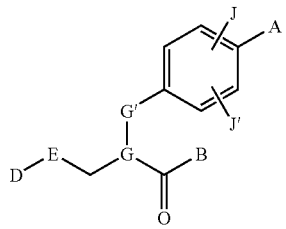

(1)

wherein A represents one of the following general formulae (2-1) to (2-6), —NR1-Z, —NR1-C(=O)-Z, —NR1-SO$_2$-Z, —NR1-C(=O)—NH-Z and —NR1-C(=S)—NH-Z, wherein R1 represents a hydrogen atom, a lower alkyl group, a lower alkenyl group, a lower alkynyl group, a lower alkyl group substituted with a cycloalkyl group(s) which may contain a hetero atom(s) in the ring thereof, a lower alkyl group substituted with an aryl group(s) or a lower alkyl group substituted with a heteroaryl group(s), R1 and Z may be bonded together to form a ring which may contain one or two oxygen, nitrogen or sulfur atoms, Z represents the following general formula (2), a lower alkyl group, a lower alkenyl group, a lower alkynyl group, a cycloalkyl group which may contain a hetero atom(s) in the ring thereof, an aryl group, a heteroaryl group, a lower alkyl group substituted with a cycloalkyl group(s) which may contain a hetero atom(s) in the ring thereof, a lower alkyl group substituted with the general formula (2), a lower alkyl group substituted with an aryl group(s), a lower alkyl group substituted with a heteroaryl group(s), a lower alkenyl group substituted with a cycloalkyl group(s) which may contain a hetero atom(s) in the ring thereof, a lower alkenyl group substituted with an aryl group(s), a lower alkenyl group substituted with a heteroaryl group(s), a lower alkynyl group substituted with a cycloalkyl group(s) which may contain a hetero atom(s) in the ring thereof, a lower alkynyl group substituted with an aryl group(s) or a lower alkynyl group substituted with a heteroaryl group(s),

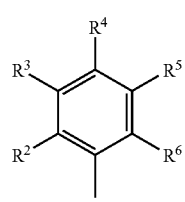

(2)

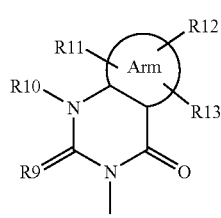

(2-1)

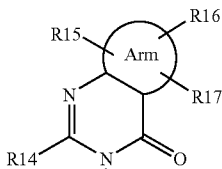

(2-2)

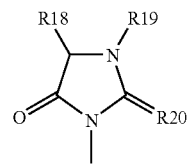

(2-3)

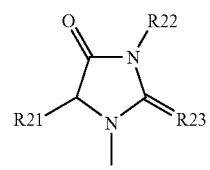

(2-4)

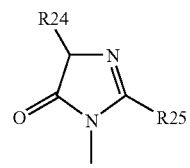

(2-5)

wherein R2 to R6, R10 to R17, R21, R22 and R24 to R28 may be the same or different from one another and each represent a hydrogen atom, a halogen atom, a hydroxyl group, a lower alkyl group, a lower alkenyl group, a lower alkynyl group, a cycloalkyl group which may contain a hetero atom(s) in the ring thereof, an aryl group, a heteroaryl group, a lower alkyl group substituted with a cycloalkyl group(s) which may contain a hetero atom(s) in the ring thereof, a lower alkyl group substituted with an aryl group(s), a lower alkyl group substituted with a heteroaryl group(s), a lower alkoxyl group, a lower alkoxyl group substituted with a cycloalkyl group(s) which may contain a hetero atom(s) in the ring thereof, a lower alkoxyl group substituted with an aryl group(s), a lower alkoxyl group substituted with a heteroaryl group(s), a cycloalkyloxy group which may contain a hetero atom(s) in the ring thereof, an aryloxy group, a heteroaryloxy group, a lower hydroxyalkyl group, a lower hydroxyalkenyl group, a lower hydroxylalkoxyl group, a lower halogenoalkyl group, a lower halogeno alkoxyl group, a lower halogenoalkenyl group, nitro group, cyano group, a substituted or unsubstituted amino group, carboxyl group, a lower alkyloxycarbonyl group, a substituted or unsubstituted carbamoyl group, a lower alkanoyl group, an aroyl group, a lower alkylthio group, a lower alkylsulfonyl group or a substituted or unsubstituted sulfamoyl group, Arm represents a benzene ring, a cyclic alkyl group or an aromatic ring containing 0, 1, 2, 3 or 4 hetero atoms selected from the group consisting of oxygen, sulfur and nitrogen atoms, R9, R20 and R23 may be the same or different from one another and each represent an oxygen atom, a substituted or unsubstituted imino group or a sulfur atom, R18 and R19 may be the same or different from one another and each represent a hydrogen atom, a lower alkyl group, a lower alkenyl group, a lower alkynyl group, a cycloalkyl group which may contain a hetero atom(s) in the ring thereof, an aryl group, a heteroaryl group, a lower alkyl group substituted with a cycloalkyl group(s) which may contain a hetero atom(s) in the ring thereof, a lower alkyl group substituted with an aryl group(s), a lower alkyl group substituted with a heteroaryl group(s), a lower alkenyl group substituted with a cycloalkyl group(s) which may contain a hetero atom(s) in the ring thereof, a lower alkenyl group substituted with an aryl group(s), a lower alkenyl group substituted with a heteroaryl group(s), a lower alkynyl group substituted with a cycloalkyl group(s) which may contain a hetero atom(s) in the ring thereof, a lower alkynyl group substituted with an aryl group(s), a lower alkynyl group substituted with a heteroaryl group(s), a lower halogenoalkyl group, a lower halogenoalkenyl group, a lower hydroxyalkyl group, a lower hydroxyalkenyl group, or a substituted or unsubstituted lower aminoalkyl group, and R18 and R19 may be bonded together to form a ring which may contain one or two oxygen, nitrogen or sulfur atoms, a substituent(s) thereof is a hydrogen atom, a halogen atom, a hydroxyl group, a lower alkyl group, a lower alkenyl group, a lower alkynyl group, a cycloalkyl group which may contain a hetero atom(s) in the ring thereof, an aryl group, a heteroaryl group, a lower alkyl group substituted with a cycloalkyl group(s) which may contain a hetero atom(s) in the ring thereof, a lower alkyl group substituted with an aryl group(s), a lower alkyl group substituted with a heteroaryl group(s), a lower alkanoyl group, an aroyl group, a lower halogenoalkanoyl group, a lower alkyloxy group, nitro group, cyano group, a substituted or unsubstituted amino group, carboxyl group, a lower alkoxyl carbonyl group, a substituted or unsubstituted carbamoyl group, a lower alkylthio group, a lower alkylsulfonyl group or a substituted or unsubstituted sulfamoyl group, B represents a hydroxyl group, a lower alkoxyl group, hydroxylamino group, amino group or a lower alkylamino group, D represents a lower alkyl group, a cycloalkyl group(s) which may contain a hetero atom(s) in the ring thereof, an aryl group or a heteroaryl group, and each may have a substituent(s), E represents C═O or CHOH, G–G' represents CH—CH2 or CH═CH2, J and J' may be same or different from one another and each represent a hydrogen atom, a halogen atom, a lower alkyl group, a lower alkyloxy group or nitro group.

The present invention provides a pharmaceutical composition and an α 4 integrin antagonist containing the above-described phenylpropionic acid derivative(s) or a pharmaceutically acceptable salt thereof as the active ingredient.

The present invention further provides a therapeutic agent or preventive agent, containing the phenylpropionic acid derivative(s) or a pharmaceutically acceptable salt thereof as the active ingredient, for diseases in which α 4 integrin-depending adhesion process participates in the pathology, such as inflammatory diseases, rheumatoid arthritis, inflammatory bowel diseases, systemic lupus erythematosus, multiple sclerosis, Sjögren's syndrome, asthma, psoriasis, allergy, diabetes, cardiovascular diseases, arterial sclerosis, restenosis, tumor proliferation, tumor metastasis and transplantation rejection.

BEST MODE FOR CARRYING OUT THE INVENTION

The term "lower" in, for example, a lower alkyl group in the present specification indicates that the group has 1 to 6 carbon atoms and preferably 1 to 4 carbon atoms. Alkyl groups, alkenyl groups and alkynyl groups in alkyl groups, alkenyl groups, alkynyl groups, alkoxyl groups, alkylthio groups, alkanoyl groups, alkylamino groups and the like may be either linear or branched. Examples of these alkyl groups are methyl group, ethyl group, propyl group, isopropyl group, butyl group, secondary butyl group, tertiary butyl group, pentyl group and hexyl group. The alkenyl groups are, for example, vinyl group, propenyl group, butenyl group and pentenyl group. The alkynyl groups include ethynyl group, propynyl group and butynyl group. The cycloalkyl groups indicate substituted or unsubstituted cycloalkyl groups such as cyclopropyl group, cyclobutyl group, cyclopentyl group, cyclohexyl group, norbornyl group, adamantyl group and cyclohexenyl group. The alkoxyl groups include methoxyl group, ethoxyl group, propyloxy group, isopropyloxy group, etc. The hetero atoms include nitrogen, oxygen, sulfur, etc. The halogen atoms are fluorine, chlorine, bromine and iodine. The halogenoalkyl groups include chloromethyl group, trichloromethyl group, trifluoromethyl group, trifluoroethyl group, pentafluoromethyl group, etc. The halogenoalkoxyl groups include trichloromethoxyl group, trifluoromethoxyl group, etc. The hydroxyalkyl groups include hydroxymethyl group, hydroxyethyl group, etc. The cycloalkyl groups which may contain a hetero atom(s) in the ring thereof may be either substituted or unsubstituted. Examples of them include piperidyl group, piperazinyl group, morpholinyl group, pyrrolidinyl group, tetrahydrofuranyl group and the groups represented by the above general formula (2-1), (2-2), (2-3), (2-4) or (2-5).

In the present specification, the aryl groups are both substituted and unsubstituted aryl groups such as phenyl group, 1-naphthyl group and 2-naphthyl group. They are preferably phenyl group and substituted phenyl group, and the substituents are particularly preferably halogen atoms, alkoxyl groups, alkyl groups, hydroxyl group, halogenoalkyl groups, halogenoalkoxyl groups, cyano group, a substituted or unsubstituted amino group, nitro group and alkylcarbonyl group. The heteroaryl groups are both substituted and unsubstituted heteroaryl groups such as pyridyl group, pyrimidinyl group, furyl group, thienyl group, indolyl group, quinolyl group and isoquinolyl group. Preferred heteroaryl groups are pyridyl group, pyrimidinyl group, furyl group, thienyl group and substituted pyridyl, pyrimidinyl, furyl and thienyl groups. Particularly preferred substituents are halogen atoms, alkoxyl groups, alkyl groups, hydroxyl group, halogenoalkyl groups, halogenoalkoxyl groups, a lower alkylthio group, a lower alkylsulfinyl group, a lower alkylsulfonyl group, a substituted or unsubstituted amino group, cyano group, nitro group and alkylcarbonyl group. The lower alkyl groups substituted with an aryl group(s) include, for example, benzyl groups and substituted benzyl groups. Particularly preferred substituents are halogen atoms, alkoxyl groups, alkyl groups, hydroxyl group, halogenoalkyl groups, halogenoalkoxyl groups, a substituted or unsubstituted amino group and alkylthio groups. The lower alkyl groups substituted with a heteroaryl group(s) include, for example, pyridylmethyl group, and particularly preferred substituents thereof are halogen atoms, alkoxyl groups, alkyl groups, hydroxyl group, halogenoalkyl groups and halogenoalkoxyl groups. The alkanoyl groups include, for example, formyl groups, acetyl groups, propanoyl group, butanoyl group and pivaloyl group. The aroyl groups include, for example, substituted or unsubstituted benzoyl group and pyridylcarbonyl group, and the substituents thereof are particularly preferably halogen atoms, alkoxyl groups, alkyl groups, hydroxyl group, halogenoalkyl groups and halogenoalkoxyl groups. The halogenoalkanoyl groups include, for example, trichloroacetyl group and trifluoroacetyl group. The alkylsulfonyl groups include, for example, methanesulfonyl group, ethanesulfonyl group, etc. The arylsulfonyl groups include, for example, benzenesulfonyl group and p-toluenesulfonyl group. The heteroarylsulfonyl groups include, for example, pyridylsulfonyl group. The halogenoalkylsulfonyl groups include, for example, trifluoromethanesulfonyl group. The alkyloxycarbonyl groups include, for example, methoxycarbonyl group, ethoxycarbonyl group and tert-butoxycarbonyl group. The aryl-substituted alkoxycarbonyl groups include, for example, benzyloxycarbonyl group and 9-fluorenylmethoxycarbonyl group. The substituted carbamoyl groups include, for example, methylcarbamoyl group, phenylcarbamoyl group and substituted phenylcarbamoyl group, and the substituents thereof are particularly preferably halogen atoms, alkoxyl groups, alkyl groups, hydroxyl group, halogenoalkyl groups and halogenoalkoxyl groups. The substituted thiocarbamoyl groups include, for example, methylthiocarbamoyl group, phenylthiocarbamoyl group and substituted phenylthiocarbamoyl groups, and the substituents thereof are particularly preferably halogens, alkoxyl groups, alkyl groups, hydroxyl group, halogenoalkyl groups and halogenoalkoxyl groups. In the present specification, the substituents in the substituted amino groups include lower alkyl groups, lower alkyl groups substituted with an aryl group, lower alkyl groups substituted with a heteroaryl group, lower alkanoyl groups, aroyl groups, lower halogenoalkanoyl groups, lower alkylsulfonyl groups, arylsulfonyl groups, heteroarylsulfonyl groups, halogenoalkylsulfonyl groups, lower alkyloxycarbonyl groups, aryl-substituted lower alkyloxycarbonyl groups, substituted or unsubstituted carbamoyl groups and substituted or unsubstituted thiocarbamoyl groups.

In the above-described general formula (1), the groups indicated as A are preferably either one of the general formulae (2-1) to (2-6), —NR1-Z, —NR1-C(=O)-Z and —NR1-SO$_2$-Z and more preferably the general formulae (2-1) to (2-6) and —NR1-C(=O)-Z. The general formula (2-1) is particularly preferable.

In the groups represented by Z, cycloalkyl groups which may contain a hetero atom(s) in the ring thereof, aryl groups and heteroaryl groups are either unsubstituted or substituted, and the substituents are those described above with reference to R2 to R6. Preferred groups represented by Z are the general formula (2), a lower alkyl group, a lower alkenyl group, a lower alkynyl group, a cycloalkyl group which may contain a hetero atom(s) in the ring thereof, an aryl group, a heteroaryl group, a lower alkyl group substituted with a cycloalkyl group(s) which may contain a hetero atom(s) in the ring thereof, a lower alkyl group substituted with the general formula (2), a lower alkyl group substituted with an aryl group(s) and a lower alkyl group substituted with a heteroaryl group(s). A lower alkyl group substituted with the general formula (2) and a substituted heteroaryl group are further preferable. A lower alkyl group substituted with the general formula (2) and heteroaryl group are also preferable.

In the above-described general formula (1), it is preferable that the groups indicated as A are both the general formulae (2-1) and (2-2), Arm in the general formulae (2-1) and (2-2) is preferably an aromatic ring and particularly a benzene ring and substituted benzene ring are preferable. R10 in the general formula (2-1) and R14 in the general formula (2-2) are preferably a hydrogen atom, a lower alkyl group and substituted lower alkyl group. Substituents thereof are preferably a phenyl group, cyano group and carboxyl group. It is preferable that R11 to R17 of the general formulae (2-1) and (2-2) are a hydrogen atom, a halogen, a hydroxyl group, a lower alkyl group, a lower alkoxy group, a lower halogenoalkyl group, a lower halogenoalkoxyl group, a substituted or unsubstituted amino group and an ammonium group.

R9 in the general formula (2-1) is preferably an oxygen atom or a sulfur atom, and more preferably an oxygen atom.

Further, in the formula (2-1), it is preferable that Arm represents a benzene ring, R9 represents an oxygen atom, R10 represents a lower alkyl group, and R11 to R13 represent a hydrogen atom, a halogen atom, a substituted or unsubstituted amino group, nitro group, a lower alkyl group, a lower alkenyl group, a hydroxyl group, or a lower alkoxyl group.

In the general formula (1), the groups represented by A are also preferably the general formulae (2-3), (2-4) and (2-5). R20 and R23 in the above formulae are preferably an oxygen atom and sulfur atom, and particularly preferably an oxygen atom. R19, R22, R24 and R25 in the above formulae are preferably a hydrogen atom, a halogen, a hydroxyl group, a lower alkyl group, a lower alkoxyl group, a lower halogenoalkyl group, a lower halogenoalkoxyl group, a substituted or unsubstituted amino group and an ammonium group.

The group represented by B is preferably a hydroxyl group or a lower alkoxyl group, and particularly preferably a hydroxyl group.

The group represented by D is preferably an aryl group and a heteroaryl group.

Here, an aryl group and a heteroaryl group are either unsubstituted or substituted, and the substituents are those described above with reference to R1, R2, R3, R4, R5, R6 and R7.

Among these, the group represented by D is preferably a phenyl group in the aryl groups, and pyridyl group in the heteroaryl groups and particularly preferably a phenyl group. The substituents thereof are preferably 1 to 3 of, more preferably, 1 or 2 of lower alkyl groups or lower alkoxyl groups or halogen atoms such as a fluorine atom and chlorine atom.

Particularly among these, the group represented by D is preferably a phenyl group or pyridyl group having the substituents on the second position and the sixth position thereof. The substituents thereof are particularly preferably a halogen atom or a lower alkyl group.

The examples are 2,6-dihalogenophenyl, 2,6-dialkylphenyl, 2-halogeno-6-alkylphenyl, 2,6-dihalogenopyridyl, 2,6-dialkylpyridyl and 2-halogeno-6-alkylpyridyl, and preferably 2,6-dichlorophenyl, 2,6-difluorophenyl, 2,6-dimethylphenyl, 2-chloro-6-methylphenyl, 2,6-dichloropyridyl, 2,6-difluoropyridyl, 2,6-dimethylpyridyl and 2-chloro-6-methylpyridyl. 2,6-dichlorophenyl and 2,6-difluorophenyl are further preferable.

The group represented by E is preferably C=O and CHOH, and more preferably a carbonyl group (C=O).

It is preferable that G–G' is CH—CH2.

The group represented by J and J' is a hydrogen atom.

It is preferable that, in the general formula (1) of the present invention, A represents either one of the general formulae (2-1) to (2-6), —NR1-Z, —NR1-C(=O)-Z and —NR1-SO$_2$-Z, Z represents the general formula (2), a lower alkyl group, a lower alkenyl group, a lower alkynyl group, a cycloalkyl group which may contain a hetero atom(s) in the ring thereof, an aryl group, a heteroaryl group, a lower alkyl group substituted with a cycloalkyl group(s) which may contain a hetero atom(s) in the ring thereof, a lower alkyl group substituted with the general formula (2), a lower alkyl group substituted with an aryl group(s) or a lower alkyl group substituted with a heteroaryl group(s), and B represents a hydroxyl group or a lower alkoxyl group.

Further, it is preferable that, in the general formula (1) of the present invention, A represents one of the general formulae (2-1) to (2-6), —NR1-Z, —NR1-C(=O)-Z, —NR1-SO$_2$-Z, —NR1-C(=O)—NH-Z and —NR1-C(=S)—NH-Z, wherein R1 represents a hydrogen atom, a lower alkyl group, a lower alkenyl group, a lower alkynyl group, a lower alkyl group substituted with a cycloalkyl group(s) which may contain a hetero atom(s) in the ring thereof, a lower alkyl group substituted with an aryl group(s) or a lower alkyl group substituted with a heteroaryl group(s), R1 and Z may be bonded together to form a ring which may contain one or two oxygen, nitrogen or sulfur atoms, Z represents the general formula (2), a lower alkyl group, a lower alkenyl group, a lower alkynyl group, a cycloalkyl group which may contain a hetero atom(s) in the ring thereof, an aryl group, a heteroaryl group, a lower alkyl group substituted with a cycloalkyl group(s) which may contain a hetero atom(s) in the ring thereof, a lower alkyl group substituted with the general formula (2), a lower alkyl group substituted with an aryl group(s), a lower alkyl group substituted with a heteroaryl group(s), a lower alkenyl group substituted with a cycloalkyl group(s) which may contain a hetero atom(s) in the ring thereof, a lower alkenyl group substituted with an aryl group(s), a lower alkenyl group substituted with a heteroaryl group(s), a lower alkynyl group substituted with a cycloalkyl group(s) which may contain a hetero atom(s) in the ring thereof, a lower alkynyl group substituted with an aryl group(s) or a lower alkynyl group substituted with a heteroaryl group(s), R2, R3, R4, R5 and R6 in the general formula (2) may be the same or different from one another and each represent a hydrogen atom, a halogen atom, a hydroxyl group, a lower alkyl group, a lower alkenyl group, a lower alkynyl group, a cycloalkyl group which may contain a hetero atom(s) in the ring thereof, an aryl group, a heteroaryl group, a lower alkyl group substituted with a cycloalkyl group(s) which may contain a hetero atom(s) in the ring thereof, a lower alkyl group substituted with an aryl group(s), a lower alkyl group substituted with a heteroaryl group(s), a lower alkoxyl group, a lower alkoxyl group substituted with a cycloalkyl group(s) which may contain a hetero atom(s) in the ring thereof, a lower alkoxyl group substituted with an aryl group(s), a lower alkoxyl group substituted with a heteroaryl group(s), a cycloalkyloxy group which may contain a hetero atom(s) in the ring thereof, an aryloxy group, a heteroaryloxy group, a lower hydroxyalkyl group, a lower hydroxyalkenyl group, a lower hydroxylalkoxyl group, a lower halogenoalkyl group, a lower halogeno alkoxyl group, a lower halogenoalkenyl group, nitro group, cyano group, a substituted or unsubstituted amino group, carboxyl group, a lower alkyloxycarbonyl group, a substituted or unsubstituted carbamoyl group, a lower alkanoyl group, an aroyl group, a lower alkylthio group, a lower alkylsulfonyl group or a substituted or unsubstituted sulfamoyl group, B represents a hydroxyl group, a lower alkoxyl group, hydroxylamino group or a lower alkylamino group, D represents a lower alkyl group, a cycloalkyl group(s) which may contain a hetero atom(s) in the ring thereof, an aryl group or a heteroaryl group, and each may have a substituent(s), and J and J' may be same or different from one another and each represent a hydrogen atom, a halogen atom, a lower alkyl group, a lower alkyloxy group or nitro group.

It is also preferable that, in the formula, A represents —NR1-C(=O)-Z,

Z represents either one of the general formula (2) wherein R2, R3, R4, R5 and R6 may be the same or different from one another and each represent a hydrogen atom or a halogen atom, a cycloalkyl group which may contain a hetero atom(s) in the ring thereof and a heteroaryl group, B represents a hydroxyl group or a lower alkoxyl group, E represents C=O, G–G' is CH—CH2, J and J' represent a hydrogen atom, and D represents a lower alkyl group, a cycloalkyl group(s) which may contain a hetero atom(s) in the ring thereof, an aryl group or a heteroaryl group which may have a substituent(s).

It is further preferable that, in the formula, A represents the general formulae (2-1) to (2-6), B represents a hydroxyl group or a lower alkoxyl group, E represents C=O, G–G' is CH—CH2, J and J' represent a hydrogen atom, and D represents a lower alkyl group, a cycloalkyl group(s) which may contain a hetero atom(s) in the ring thereof, an aryl group or a heteroaryl group which may have a substituent(s).

It is preferable that, in the general formula (2-1), Arm represents a benzene ring, R9 represents an oxygen atom, R10 represents a lower alkyl group, and R11 to R13 represent a hydrogen atom, a halogen atom, a substituted or unsubstituted amino group, nitro group, a lower alkyl group, a lower alkenyl group, a hydroxyl group, or a lower alkoxyl group, and particularly preferably a hydrogen atom, a halogen atom, a substituted or unsubstituted amino group or nitro group.

The phenylpropionic acid derivatives (1) of the present invention can be synthesized by methods described below. For example, in the general formula (1), a phenylpropionic acid derivative (9) can be synthesized as follows when -A represents a group(s) defined as Q mentioned below and B represents a hydroxyl group.

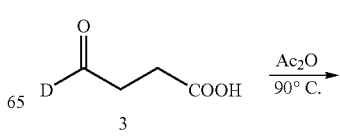

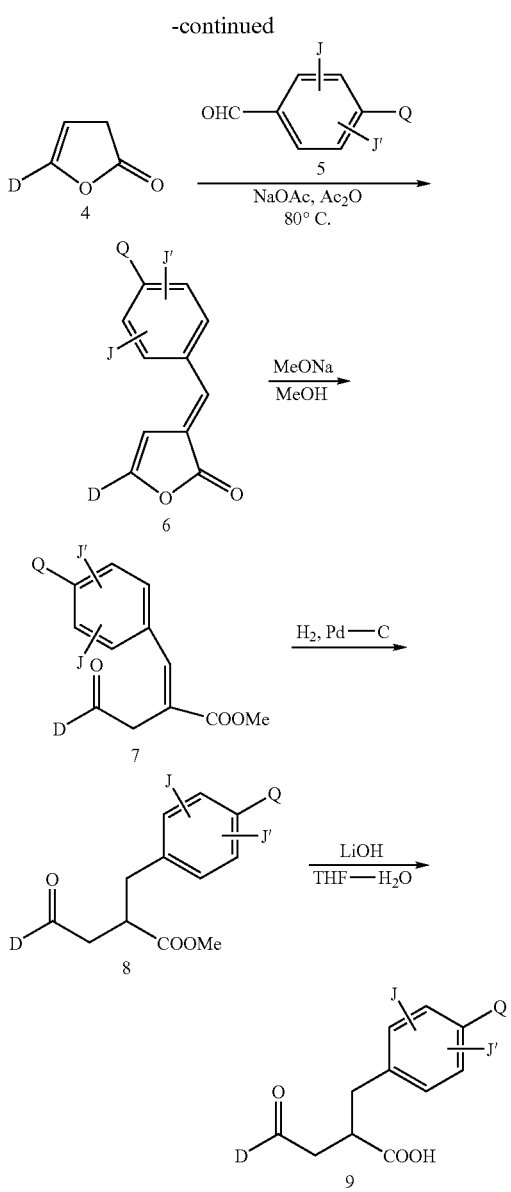

A carboxylic acid (3) is heated in acetic anhydride to obtain a lactone (4) and the lactone (4) is condensed with benzaldehyde (5). After ring-opening of benzylidene (6), hydrogenation and ester hydrolysis, a phenylpropionic acid (9) can be produced.

Further, an olefin body (7) or an ester body (8) can be converted to alcohol by reducing a carbonyl group with suitable reducing agents.

Hereat, the substituent Q of the benzaldehyde (5) has a structure of -A as described above with reference to the general formula (1), it is a substituent which can be converted into -A in any stage of the synthesis or it is suitably protected form of these substituents.

A carboxylic acid (9) can be obtained by applying purification methods such as column chromatography, HPLC and recrystallization to the thus-obtained phenylpropionic acid (9).

The compound wherein B represents a lower alkoxyl group in the general formula (1) can be obtained by condensing the carboxylic acid (9) with a suitable lower alcohol under the existence of a suitable condensing agent or acid catalyst.

The compound wherein B represents a hydroxylamino group in the general formula (1) can be obtained by condensing the carboxylic acid (9) with a hydroxylamine under the existence of a suitable condensing agent.

In the above procedure, the compound wherein B represents an amino group or a lower alkylamino group in the general formula (1) can be obtained by condensing an amine or a lower alkylamine instead of hydroxylamine under the existence of a suitable condensing agent.

The structures represented by a building block -A of the general formula (1) can be synthesized from the corresponding precursors in accordance with the following reactions. In the following reactions, the precursor Q can be converted to -A in a suitable stage of a usual synthesizing method of the general formula (1).

When Q has a hydroxyl group or a properly protected hydroxyl group, if necessary, after the protecting group-removing reaction, Q can be converted as follows.

A hydroxyl group in Q can form various ether structures by reacting with an alkylating agent such as alkyl halide and alkyl sulfonate in an organic solvent under the existence of a suitable base. Ether compounds can also be obtained by Mitsunobu reaction, in which the hydroxyl group is reacted with various alcohols under the existence of dialkylazodicarboxylic acid. Various arylether and heteroarylether structures can be formed by reacting with aryl or heteroaryl halide or with aryl or heteroaryl boronic acid in an organic solvent under the existence of a suitable base or catalyst.

The hydroxyl group in Q can form the corresponding sulfonic ester structure by reacting sulfonic acid halide and sulfonic anhydrides in an organic solvent such as DMF and dichloromethane under the existence of an organic base such as triethylamine, diisopropylethylamine, pyridine and N,N-dimethylaminopyridine or an inorganic base such as potassium carbonate and sodium carbonate.

Trifluoromethanesulfonic ester (hereinafter referred to as triflate) can be obtained in accordance with the above reaction condition of sulfonation. The triflate can be converted to aryl-substituted and heteroaryl-substituted forms by Suzuki coupling reaction, which is a reaction with the various boronic acids using a palladium catalyst such as tetrakistriphenylphosphine palladium and palladium acetate or other metal catalysts under warming or at room temperature in a solvent such as DMF, DME (1,2-dimethoxyethane), toluene and dioxane. Other than triflate, the compounds wherein Q is substituted with a halogen atom can also be converted to the aryl-substituted forms in the above conversion reaction.

When Q has a properly protected amino group, an amino group can be produced by respective protecting group-removing reaction, the methods of which are different according to protecting groups. When Q has a nitro group, an amino group can be produced by hydrogenation using a metal catalyst or reduction using a reducing agent. The thus-obtained amino group can further lead to the various structures by the following reactions.

The amino group can be converted to an alkylamino group by reacting with an alkylating agent such as alkyl halide and alkyl sulfonate in an organic solvent under the existence of a suitable base. An arylamine structure can be formed by reacting the amino group with aryl halide in an organic solvent under the existence of a suitable base.

The amino group can also be converted to an alkylamino group by reacting with various aldehyde and ketones in a solvent such as DMF, dichloromethane, trialkyl orthoformate and trialkyl orthoacetate under the existence of a reducing agent such as sodium borohydride and sodium cyanoborohydride. The above amino or alkylamino group can further lead to the various structures by the following reactions.

The amino or alkylamino group can form the corresponding amide and sulfonamide structures by reacting carboxylic acid halide, carboxylic anhydrides, sulfonic acid halide and sulfonic anhydrides in an organic solvent such as DMF and dichloromethane under the existence of an organic base such as triethylamine, diisopropylethylamine, pyridine and N,N-dimethylaminopyridine or an inorganic base such as potassium carbonate and sodium carbonate. The amide structure can also be formed by reacting a carboxylic acid in an organic solvent such as DMF and dichloromethane under the existence of a suitable additive agent and condensing agent.

The amino or alkylamino group can form the corresponding urea or thiourea structure by reacting with various isocyanate and isothiocyanate in an organic solvent such as DMF, toluene and dichloromethane under the existence of an organic base such as triethylamine, diisopropylethylamine, pyridine and N,N-dimethylaminopyridine, if necessary.

An amide body can be obtained by reacting the amino group with a suitably protected aminocarboxylic acid in an organic solvent such as DMF and dichloromethane under the existence of a suitable additive agent and condensing agent. The amide body can also be obtained by reacting the amino group with a suitably protected aminocarboxylic acid halide under the existence of a suitable base. After the protecting group-removing reaction, the closed circular compounds can be obtained by reacting the amide body with 1,1-carbonyldiimidazole or trimethyl orthoformate. N-alkyl body of the closed circular compounds can be synthesized by alkylation thereof under a suitable condition.

Alkylation can be conducted from the sulfonamide structure by the Mitsunobu reaction using an alcohol. Alkylation can also be conducted by reacting the sulfonamide structure with an alkylating agent such as alkyl halide and alkyl sulfonate, in an organic solvent under the existence of a suitable base. When using isocyanates and isothiocyanates having a leaving group on a suitable position on forming the urea or thiourea structure, the closed circular compounds can be obtained by treating the formed urea or thiourea compound with a base and the like. Those compounds can be N-alkylated under a suitable condition.

Because the phenylpropionic acid derivatives of the general formula (1) of the present invention include asymmetric carbons, it can be considered that the phenylpropionic acid derivatives of the general formula (1) of the present invention are optical isomers and the compound indicated in the present invention include the said optical isomers. Regarding the compound in which a diastereomer exists, the diastereomer and the diastereomer mixture are included in the said phenylpropionic acid derivatives. Because the phenylpropionic acid derivatives of the general formula (1) of the present invention include a movable hydrogen atom, it can be considered that the phenylpropionic acid derivatives of the general formula (1) of the present invention include a variety of tautomeric forms and the compounds indicated in the present invention include the said tautomeric forms. Further, the carboxyl groups of the compound of the present invention may be substituted with appropriate substituents which are converted into a carboxyl group in vivo. An example of such substituents is a lower alkoxycarbonyl group. More concretely, they include methoxycarbonyl group, ethoxycarbonyl group, isopropoxycarbonyl group and the like.

When the compounds of general formula (1) can form salts thereof, it is sufficient for the salts to be pharmaceutically acceptable ones. When the compound has an acidic group such as carboxyl group, the salts can be ammonium salts, or salts thereof with alkali metals, e.g. sodium and potassium, salts thereof with alkaline earth metals, e.g. calcium and magnesium, salts thereof with aluminum and zinc, salts thereof with organic amines, e.g. triethylamine, ethanolamine, morpholine, piperidine and dicyclohexylamine, and salts thereof with basic amino acids, e.g. arginine and lysine. When the compound has a basic group, the salts can be those with inorganic acids, e.g. hydrochloric acid, sulfuric acid and phosphoric acid; those with organic-carboxylic acids, e.g. acetic acid, citric acid, benzoic acid, maleic acid, fumaric acid, tartaric acid and succinic acid; and those with organosulfonic acids, e.g. methanesulfonic acid and p-toluenesulfonic acid. The salts can be formed by mixing a compound of the general formula (1) with a necessitated acid or base in a proper ratio in a solvent or dispersant or by the cation exchange or anion exchange reaction with another salt.

The compounds of the general formula (1) of the present invention include also solvates thereof such as hydrates and alcohol adducts thereof.

The compounds of general formula (1) and salts thereof are administered as they are or in the form of various pharmaceutical compositions to patients. The dosage forms of the pharmaceutical compositions are, for example, tablets, powders, pills, granules, capsules, suppositories, solutions, sugar-coated tablets, depots and syrups. They can be prepared with ordinary preparation assistants by an ordinary method.

For example, the tablets are prepared by mixing the phenylpropionic acid derivative, the active ingredient of the present invention, with any of known adjuncts such as inert diluents, e.g. lactose, calcium carbonate and calcium phosphate; binders, e.g. acacia, corn starch and gelatin; extending agents, e.g. alginic acid, corn starch and pre-gelatinized starch; sweetening agents, e.g. sucrose, lactose and saccharin; flavour, e. g. peppermint, Akamono (Gaultheria aderothrix) Oil and cherry; lubricants, e.g. magnesium stearate, talc and carboxymethyl cellulose; excipients for soft gelatin capsules and suppositories, e.g. fats, waxes, semi-solid or liquid polyols, natural oils and hardened oils; and excipients for solutions, e.g. water, alcohols, glycerols, polyols, sucrose, invert sugars, glucose and vegetable oils.

The antagonist containing a compound(s) of above general formula (1) or a salt(s) thereof as active ingredient is usable as a therapeutic agent or preventing agent for diseases in which α 4 integrin-depending adhesion process participates in the pathology, such as inflammatory diseases, rheumatoid arthritis, inflammatory bowel diseases, systemic lupus erythematosus, multiple sclerosis, Sjögren's syndrome, asthma, psoriasis, allergy, diabetes, cardiovascular diseases, arterial sclerosis, restenosis, tumor proliferation, tumor metastasis, transplantation rejection, etc. The inflammatory bowel diseases include Crohn's disease and ulcerative colitis.

The dose of the compound of general formula (1) or salt thereof used for the above-described purpose varies depending on the intended therapeutic effect, administration method, period of the treatment, and age and body weight of the patient. The dose is usually 1 μg to 5 g a day for adults

EXAMPLES

The following Examples will further illustrate the present invention, which are only preferred embodiments of the invention and which by no means limit the invention.

Example 1

Synthesis of 4-phenyl-2-[4-(1-methyl-2,4-dioxo-1,2,3,4-tetrahydroquinazoline-3-yl)benzyl]-4-oxobutanoic acid (10)

The compound 10 was synthesized in accordance with the following scheme.

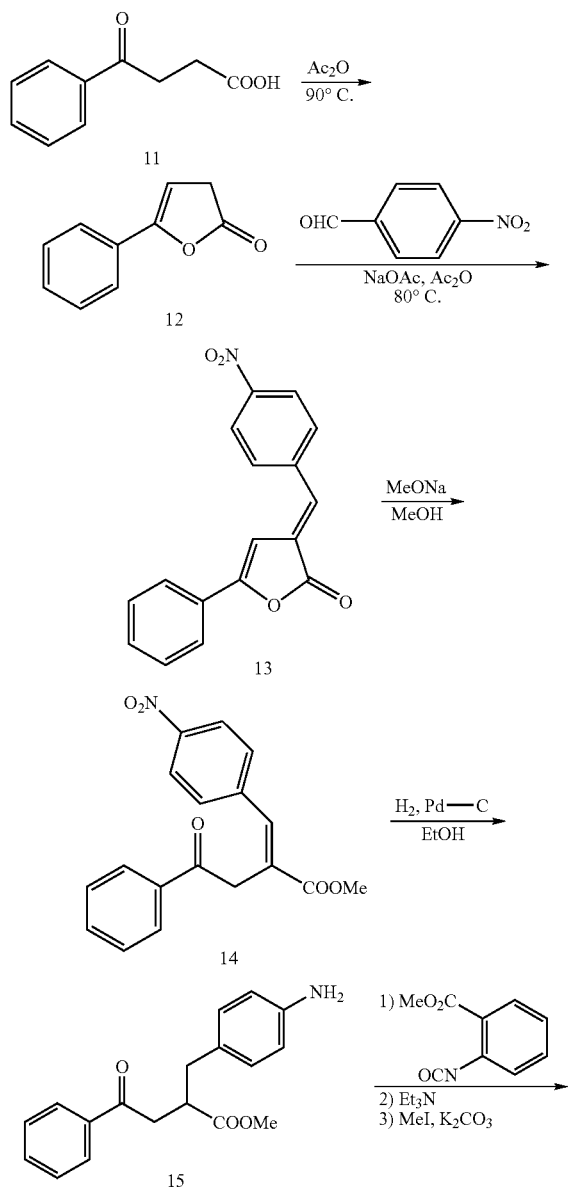

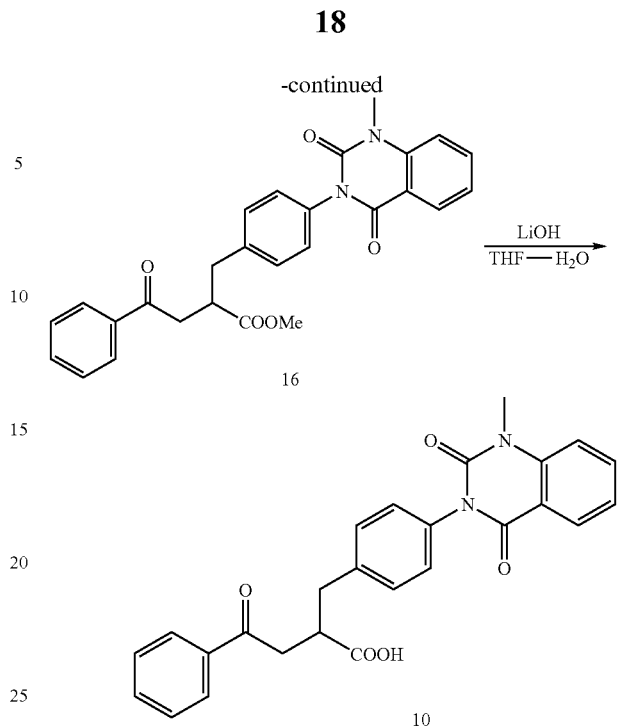

Namely, 1.80 g (10.1 mmol) of 3-benzoylpropionic acid (11) was heated at 90° C. for 5 hours in 10 ml of acetic anhydride. After removing the solvent, the reaction mixture was purified by silica gel column chromatography (hexane:ethyl acetate=10:1) to obtain 705 mg (43%) of a lactone body 12.

464 mg (3.07 mmol) of p-nitrobenzaldehyde, 227 mg (2.76 mmol) of sodium acetate and 10 ml of acetic anhydride were added to 402 mg (2.51 mmol) of the lactone body 12 and heated at 80° C. for an hour. After adding ethyl acetate and water to dilute the reaction solution, the precipitated solid material was filtered by being vacuum dried to obtain 688 mg (93%) of a benzylidene body 13.

The benzylidene 13 was dissolved in 5 ml of methanol and 464 mg (28% methanol solution, 2,40 mmol) of sodium methoxide was diluted with 2 ml of methanol and then added thereto. After an hour, the solid material which was precipitated by adding water was filtered by being vacuum dried to obtain 631 mg (84%) of a methyl ester body 14.

Further, 58.5 mg of 7.5% Pd—C(wet) and 10 ml of ethanol were added to 305 mg of the ester body 14 and reacted under hydrogen gas atmosphere for 6 hours. After Celite filtration and removing the solvent, the residue was purified by silica gel chromatography (hexane:ethyl acetate=2:1) to obtain 77.8 mg (28%) of a reductant 15.

44.0 mg (0.25 mmol) of methyl 2-isocyanatebenzoate and 2 ml of acetonitrile were added to 77.8 mg (0.26 mmol) of the reductant 15 and heated to 70° C. After 2 hours, triethylamine (43.5 mg, 0.31 mmol) was added and reacted at 70° C. for 11 hours. Then the precipitated material was filtered by being vacuum dried to obtain 50.8 mg of a ring product. After removing the solvent of the filtrate, the residue was purified by silica gel chromatography (hexane:ethyl acetate=2:1-1:1) to obtain 41.6 mg (total 80%) of a ring product. 92.4 mg (0.21 mmol) in total of the ring product was dissolved in 3 ml of DMF. 34.1 mg (0.25 mmol) of potassium carbonate and 68.0 mg (0.48 mmol) of methyl iodide were added and stirred for an hour. After removing DMF, the mixture was diluted with ethyl acetate and water to separate the ethyl acetate layer. The water layer was further extracted with ethyl acetate and mixed with the previously separated ethyl acetate layer, and washed with saturated NaCl aqueous solution, and dried with anhydrous sodium sulfate. The solvent was removed to obtain 99.2 mg (quant.) of a methyl ester body 16.

88.1 mg (0.19 mmol) of the methyl ester body 16 was dissolved in 2 ml of THF and 0.4 ml of water and 12.8 mg (0.31 mmol) of lithium hydroxide-monohydrate was added and stirred for 5 hours. After removing THF under reduced pressure, the mixture was diluted with ethyl acetate and an aqueous solution of saturated sodium hydrogen carbonate to separate the water layer. The ethyl acetate layer was further extracted with water and mixed with the previously separated water layer, and acidified with 1N—HCl and extracted with ethyl acetate. The ethyl acetate layer was washed with saturated NaCl aqueous solution and dried with anhydrous sodium sulfate. After removing the solvent, the residue was purified by silica gel chromatography (methylene chloride:methanol=100:1–40:1) to obtain 46.1 mg (54%) of the compound 10.

$^1$H-NMR (300 MHz, CD$_3$OD) δ 2.93 (1H, dd, J=14 and 8 Hz), 3.09 (1H, dd, J=18 and 4 Hz), 3.21 (1H, dd, J=14 and 6 Hz), 3.34 (1H, s), 3.45 (1H, dd, J=18 and 9 Hz), 3.62 (3H, s), 7.22 (2H, d, J=8 Hz), 7.33 (1H, t, J=8 Hz), 7.45 (5H, m), 7.59 (1H, t, J=7 Hz), 7.81 (1H, ddd, J=8, 7 and 2 Hz), 7.94 (2H, d, J=8 Hz), 8.15 (1H, d, J=8 and 2 Hz). MS (ESI) m/z 441 (M−H)$^-$ Example 2

Synthesis of 4-(2,6-dichlorophenyl)-2-[4-(1-methyl-2,4-dioxo-1,2,3,4-tetrahydroquinazoline-3-yl)benzyl]-4-oxobutanoic acid (17)

The compound 17 was synthesized in accordance with the following scheme.

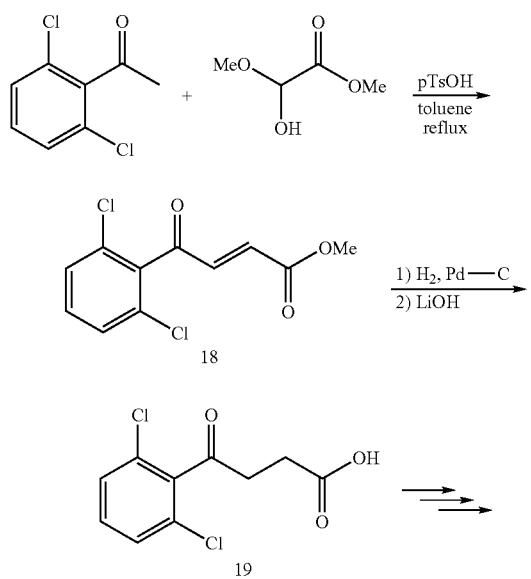

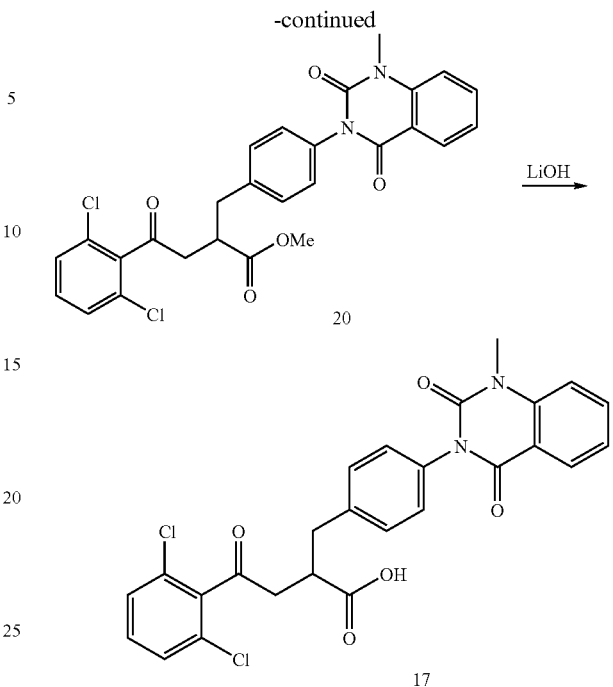

Namely, 4.39 g (23.2 mmol) of 2,6-dichloroacetophenone was refluxed in toluene under the mixed catalyst of methyl 2-hydroxy-2-methoxy acetate (3.35 g, 27.9 mmol) and p-toluenesulfonic acid (tosil acid)-monohydrate (168 mg, 0.88 mmol). Ethyl acetate and water were added to the reaction solution and diluted to separate the ethyl acetate layer. Then the ethyl acetate layer was washed with an aqueous solution of saturated sodium hydrogen carbonate and saturated NaCl aqueous solution, and dried with anhydrous sodium sulfate. After removing the solvent, the residue was purified by silica gel chromatography (hexane:ethyl acetate=25:1) to obtain 2.50 g (42%) of an ester body 18.

The ester body 18 (2.50 g) was stirred under the catalyst of 259 mg (50% wet) of 7.5% Pd—C under hydrogen gas atmosphere for 2 hours. After Celite filtration and removing the solvent, 807 mg (19.2 mmol) of lithium hydroxide-monohydrate, 60 ml of THF and 12 ml of water were added and stirred for 4 hours. After removing THF under reduced pressure, the mixture was diluted with ethyl acetate and water to separate the water layer. The water layer was acidified by adding 1N—HCl and the precipitated solid material was filtered by being vacuum dried to obtain 2.18 g (92%) of 3-(2,6-dichlorobenzoyl)propionic acid (19).

$^1$H-NMR (300 MHz, DMSO-d$_6$) δ 2.57 (2H, t, J=7 Hz), 3.10 (2H, t, J=7 Hz), 7.54 (3H, m). MS (ESI) m/z 245 (M−H)$^-$

After that, methyl ester 4-(2,6-dichlorophenyl)-2-[4-(1-methyl-2,4-dioxo-1,2,3,4-tetrahydroquinazoline-3-yl)benzyl]-4-oxobutanoic acid (20) was synthesized in the same manner as that of Example 1.

$^1$H-NMR (300 MHz,CDCl$_3$) δ 3.20 (5H, m), 3.64 (3H, s), 3.70 (3H, s), 7.28 (9H, m), 7.73 (1H, td, J=8 and 2 Hz), 8.25 (1H, dd, J=8 and 2 Hz). MS (ESI) m/z 525 (MH)$^+$ The compound 17 was synthesized from the compound 20 by hydrolysis with lithium hydroxide-monohydrate, which is the same manner as that of Example 1.

¹H-NMR (300 MHz,CDCl₃) δ 3.20 (5H, m), 3.63 (3H, s), 7.26 (7H, m), 7.40 (2H, d, J=8 Hz), 7.72 (1H, td, J=8 and 2 Hz), 8.25 (1H, dd, J=8 and 2 Hz). MS (ESI) m/z 509 (M−H)⁻

Example 3

Synthesis of 4-(2,6-difluorophenyl)-2-[4-(1-methyl-2,4-dioxo-1,2,3,4-tetrahydroquinazoline-3-yl)benzyl]-4-oxobutanoic acid (21)

The compound 21 was synthesized in accordance with the following scheme.

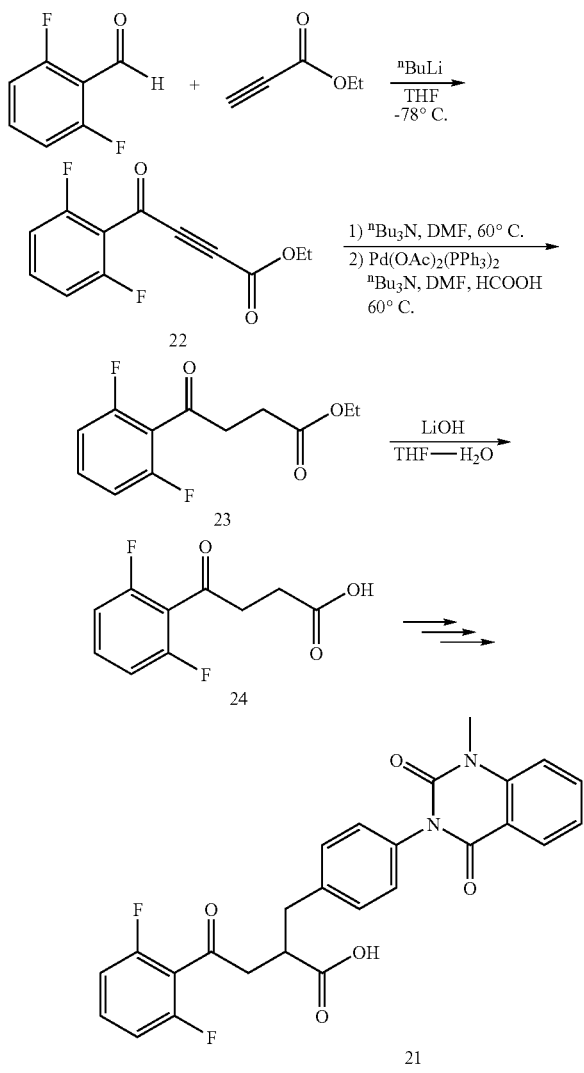

Namely, 6.88 ml (11.0 mmol) of 1.6M n-butyllithium THF solution was added dropwise at −78° C. to a solution wherein 1.01 ml (10.0 mmol) of ethyl propionate was dissolved in 20 ml of THF. After 20 minutes, a solution of 1.74 g (12.2 mmol) of 2,6-difluorobenzaldehyde in THF (5 ml) was slowly added dropwise thereto. After 2 hours, 2 ml of acetic acid was added to stop the reaction. Ethyl acetate and water were added to dilute the reaction solution and the ethyl acetate layer was separated. The water layer was further extracted with ethyl acetate and mixed with the previously separated ethyl acetate layer. Then the mixture was washed with an aqueous solution of sodium hydrogen carbonate and saturated NaCl aqueous solution, and dried with anhydrous sodium sulfate. The solvent was removed and the residue was purified by silica gel chromatography (hexane:ethyl acetate=10:1-7:1) to obtain 1.24 g (52%) of an ester body 22.

The ester body 22 (1.24 g, 5.16 mmol) and 6.15 ml (25.8 mmol) of tri-n-butylamine were stirred in 15 ml of DMF for 3 hours at 60° C. Then bis(triphenylphosphine)palladium acetate (86.6 mg, 0.12 mmol) and formic acid (0.78 ml, 20.7 mmol) were added and stirred at 60° C. After an hour, DMF was removed under reduced pressure and 1N—HCl was added and extracted with diethyl ether. The organic layer was washed with saturated NaCl aqueous solution and dried with anhydrous sodium sulfate. The solvent was removed and the residue was purified by silica gel chromatography (hexane:ethyl acetate=19:1) to obtain 719 mg (58%) of the compound 23.

After that, the compound 21 was synthesized in the same manner as that of Example 1.

¹H-NMR (300 MHz,CDCl₃) δ 3.20 (5H, m), 3.62 (3H, s), 6.94 (2H, t, J=8 Hz), 7.30 (7H, m), 7.73 (1H, td, J=8 and 2 Hz), 8.24 (1H, dd, J=8 and 2 Hz). MS (ESI) m/z 477 (M−H)⁻

Example 4

Synthesis of 4-(4-chlorophenyl)-2-[4-(1-methyl-2,4-dioxo-1,2,3,4-tetrahydroquinazoline-3-yl)benzyl]-4-oxobutanoic acid The subject compound was obtained in the same manner as that of Example 1 except that 3-(4-chlorobenzoyl)propionic acid was used as a raw material.

¹H-NMR (300 MHz,CDCl₃) δ 2.98 (2H, m), 3.34 (3H, m), 3.63 (3H, s), 7.32 (8H, m), 7.73 (1H, td, J=8 and 2 Hz), 7.87 (2H, d, J=8 Hz), 8.24 (1H, dd, J=8 and 2 Hz). MS (ESI) m/z 475 (M−H)⁻

Example 5

(E)-2-[2-(2,6-dichlorophenyl)-2-oxoethyl]-3-[4-(1-methyl-2,4-dioxo-1,2,3,4-tetrahydroquinazoline-3-yl)phenyl]acrylic acid Process 1 methyl ester (E)-2-[2-(2,6-dichlorophenyl)-2-oxoethyl]-3-[4-nitrophenyl]acrylic acid The subject compound was obtained in the same manner as that of the compound 14 (Example 1) except that the compound 19 was used as a raw material.

Process 2 methyl ester (E)-2-[2-(2,6-dichlorophenyl)-2-oxoethyl]-3-[4-aminophenyl]acrylic acid The mixture of 135 mg of methyl ester (E)-2-[2-(2,6-dichlorophenyl)-2-oxoethyl]-3-[4-nitrophenyl]acrylic acid, 20 mg of 7.5% palladium/carbon and 9 ml of ethyl acetate was stirred under hydrogen atmosphere. After Celite filtration of the reaction solution and removing the solvent, the subject compound was obtained.

MS (ESI) m/z 364 (MH)⁺

Process 3 (E)-2-[2-(2,6-dichlorophenyl)-2-oxoethyl]-3-[4-(1-methyl-2,4-dioxo-1,2,3,4-tetrahydroquinazoline-3-yl)phenyl]acrylic acid The subject compound was obtained in the same manner as that of the compound 10 (Example 1) except that methyl ester (E)-2-[2-(2,6-dichlorophenyl)-2-oxoethyl]-3-[4-aminophenyl]acrylic acid was used as a raw material.

$^1$H-NMR (300 MHz, DMSO-d$_6$) δ 3.55 (3H, s), 4.15 (2H, s), 7.25–7.40 (3H, m), 7.40–7.60 (6H, m), 7.80 (1H, t), 7.95 (1H, s), 8.05 (1H, d). MS (ESI) m/z 509 (MH)$^+$

Example 6

4-(2,6-dichlorophenyl)-2-[4-[[(2-methoxycarbonylphenyl) amino]carbonylamino]benzyl]-4-oxobutanoic acid The subject compound was obtained in the same manner as that of the compound 17 (Example 2).
MS (ESI) m/z 529 (MH)$^+$

Example 7

4-(2,6-dichlorophenyl)-4-hydroxy-2-[4-(1-methyl-2,4-dioxo-1,2,3,4-tetrahydroquinazoline-3-yl)benzyl] butanoic acid Process 1 3-[4-[[5-(2,6-dichlorophenyl)-2-oxotetrahydrofuran-3-yl]methyl]phenyl]-1-methylquinazoline-2,4-dione The mixture of 100 mg of methyl ester 4-(2,6-dichlorophenyl)-2-[4-(1-methyl-2,4-dioxo-1,2,3,4-tetrahydroquinazoline-3-yl)benzyl]-4-oxobutanoic acid (20), 3 mg of sodium borohydride, 5 ml of tetrahydrofuran and 1 ml of water was stirred. The reaction mixture was after-treated with an ordinary method using ethyl acetate as an extracting solvent. The obtained residue was purified by reverse phase HPLC to obtain the subject compound.
MS (ESI) m/z 495 (MH)$^+$ Process 2 4-(2,6-dichlorophenyl)-4-hydroxy-2-[4-(1-methyl-2,4-dioxo-1,2,3,4-tetrahydroquinazoline-3-yl)benzyl] butanoic acid The mixture of 7 mg of 3-[4-[[5-(2,6-dichlorophenyl)-2-oxotetrahydrofuran-3-yl]methyl]phenyl]-1-methylquinazoline-2,4-dione, 0.6 mg of lithium hydroxide-monohydrate and 5 ml of tetrahydrofuran was stirred. After removing a solvent, the residue was purified by reverse phase HPLC to obtain the subject compound.
MS (ESI) m/z 513 (MH)$^+$

Examples 8 to 13

The following compounds can be easily produced in the same manner as that of the Example (the compound 17, Example 2) or the above-mentioned producing methods, or by applying the methods well-known to those skilled in the art.

Example 8

4-(2,6-dichlorophenyl)-2-[4-(1-methyl-2,4-dioxo-5-chloro-1,2,3,4-tetrahydroquinazoline-3-yl)benzyl]-4-oxobutanoic acid

Example 9

4-(2,6-dichlorophenyl)-2-[4-(1-methyl-2,4-dioxo-6-chloro-1,2,3,4-tetrahydroquinazoline-3-yl)benzyl]-4-oxobutanoic acid

Example 10

4-(2,6-dichlorophenyl)-2-[4-(1-methyl-2,4-dioxo-6-nitro-1,2,3,4-tetrahydroquinazoline-3-yl)benzyl]-4-oxobutanoic acid

Example 11

4-(2,6-dichlorophenyl)-2-[4-(1-methyl-2,4-dioxo-6-dimethylamino-1,2,3,4-tetrahydroquinazoline-3-yl) benzyl]-4-oxobutanoic acid

Example 12

4-(2,6-dichlorophenyl)-2-[4-(1-methyl-2,4-dioxo-7-fluoro-1,2,3,4-tetrahydroquinazoline-3-yl)benzyl]-4-oxobutanoic acid

Example 13

4-(2,6-dichlorophenyl)-2-[4-(1-methyl-2,4-dioxo-5,8-dichloro-1,2,3,4-tetrahydroquinazoline-3-yl)benzyl]-4-oxobutanoic acid The structural formulae of the compounds obtained in Examples 1 to 13 are shown below.

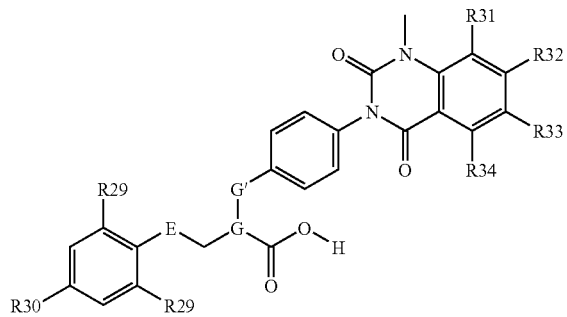

| Examples | E | G—G' | R29 | R30 | R31 | R32 | R33 | R34 |
|---|---|---|---|---|---|---|---|---|
| 1 | C=O | CH—CH2 | H | H | H | H | H | H |
| 2 | C=O | CH—CH2 | Cl | H | H | H | H | H |
| 3 | C=O | CH—CH2 | F | H | H | H | H | H |
| 4 | C=O | CH—CH2 | H | Cl | H | H | H | H |
| 5 | C=O | CH=CH | Cl | H | H | H | H | H |
| 7 | CHOH | CH—CH2 | Cl | H | H | H | H | H |
| 8 | C=O | CH—CH2 | Cl | H | H | H | H | Cl |
| 9 | C=O | CH—CH2 | Cl | H | H | H | Cl | H |
| 10 | C=O | CH—CH2 | Cl | H | H | H | NO2 | H |
| 11 | C=O | CH—CH2 | Cl | H | H | H | NMe2 | H |
| 12 | C=O | CH—CH2 | Cl | H | H | F | H | H |
| 13 | C=O | CH—CH2 | Cl | H | Cl | H | H | Cl |

Example 6

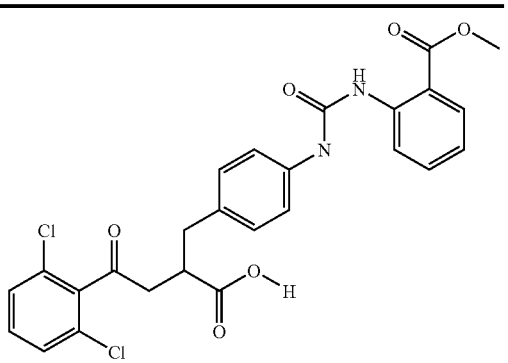

(Test Example) VCAM Antagonist Activity (VCAM-1/α 4 β 1 Binding assay)

The capacity of a test substance antagonistic to the binding of cell strain Jurkat (ATCC TIB-152) of human T cells, known to express integrin α 4 β 1, to VCAM-1 was determined.

100 µl/well of a solution (500 ng/ml) of recombinant human VCAM-1 (R & D systems) solution diluted with buffer A (0.1 M NaHCO$_3$, pH 9.6) was added to a micro titer plate having 96 wells (Nunc Maxisorp). After the incubation at 4° C. overnight, unbound VCAM-1 was removed by washing once with PBS. After completion of the washing, a buffer (buffer B) obtained by diluting Block Ace (Dainippon Pharmaceutical Co., Ltd.) with PBS to ¼ concentration was added in an amount of 150 µl/well. After the incubation at room temperature for 1 hour, buffer B was removed and the plate was washed with PBS once.

Jurkat cells were washed with Dulbecco modified Eagle medium (SIGMA, hereinafter referred to as "DMEM") twice and then incubated in DMEM containing 10 µg/ml of Calcein-AM (Wako Pure Chemical Industries, Ltd.) at 37° C. in dark place for 30 minutes to label with fluorescence. The cells were again suspended in a binding buffer (20 mM HEPES, DMEM containing 0.1% BSA).

50 µl of a test substance of various concentrations obtained by the dilution with the binding buffer was added to the plate. Immediately thereafter, 50 µl (final volume: 100 µl/well) of the fluorescent Jurkat cells (4×10$^6$ cells/ml) were added thereto, and they were incubated at room temperature for 30 minutes. After the shaking on a plate shaker (IKA MTS-4) at 800 rpm for 30 seconds, the solution was immediately removed to remove the unbound cells. The fluorescence quantity of the bound cells remaining in the wells was determined with a fluorescent plate reader (Wallac 1420 ARVO multi-label counter) (filter excitation wave length: 485 nm, emission wave length: 535 nm). The fluorescent strength thus obtained is proportional to the number of Jurkat cells bound to VCAM-1 and remaining on the plate. The binding rate of each test material in various concentrations was determined while the fluorescent strength of the test material-free well was determined to be 100%. The concentration IC$_{50}$ for the 50% binding inhibition was calculated and it was confirmed that the test substance exhibited an antagonistic activity.

(Test Example) VCAM Antagonistic Activity (VCAM-1/α 4 β 7 Binding Assay)

The capacity of a test substance antagonistic to the binding of lymphoma cell strain RPMI-8866 of human B cells, known to express integrin α 4 β 7, to VCAM-1 was determined.

100 µl/well of a solution (500 ng/ml) of recombinant human VCAM-1 (R & D systems) solution diluted with buffer A (0.1 M NaHCO$_3$, pH 9.6) was added to a micro titer plate having 96 wells (Nunc Maxisorp). After the incubation at 4° C. overnight, unbound VCAM-1 was removed by washing once with PBS. After completion of the washing, a buffer (buffer B) obtained by diluting Block Ace (Dainippon Pharmaceutical Co., Ltd.) with PBS to ¼ concentration was added in an amount of 150 µl/well. After the incubation at room temperature for 1 hour, buffer B was removed and the plate was washed with PBS once.

RPMI-8866 cells were incubated in Dulbecco modified Eagle medium containing 10 µg/ml of Calcein-AM (Wako Pure Chemical Industries, Ltd.) (SIGMA, hereinafter referred to as "DMEM") at 37° C. for 30 minutes to label with fluorescence. The cells were again suspended in a binding buffer (20 mM HEPES, DMEM containing 0.1% BSA) containing 4 mM of MnCl$_2$.

50 µl of a test substance of various concentrations obtained by the dilution with the binding buffer was added to the plate. Immediately thereafter, 50 µl (final volume: 100 µl/well) of the fluorescent RPMI-8866 cells (4×10$^6$ cells/ml) were added thereto, and they were incubated at room temperature for 30 minutes. After the shaking on a plate shaker (IKA MTS-4) at 800 rpm for 30 seconds, the solution was immediately removed to remove the unbound cells. The fluorescence quantity of the bound cells remaining in the wells was determined with a fluorescent plate reader (Wallac 1420 ARVO multi-label counter) (filter excitation wave length: 485 nm, emission wave length: 535 nm). The fluorescent strength thus obtained is proportional to the number of RPMI-8866 cells bound to VCAM-1 and remaining on the plate. The binding rate of each test material in various concentrations was determined while the fluorescent strength of the test material-free well was determined to be 100%. The concentration IC$_{50}$ for the 50% binding inhibition was calculated.

The obtained test results are shown in Table 1. The antagonistic activity is shown as A when IC$_{50}$ is 0.8 µmol/L or less, B when IC$_{50}$ is above 0.8 µmol/L and 4 µmol/L or less, C when IC$_{50}$ is above 4 µmol/L and 20 µmol/L or less, and D when IC$_{50}$ is above 20 µmol/L and 100 µmol/L or less.

TABLE 1

| Results of the determination of VCAM antagonistic activity (IC50, µmol/L): 100 ≧ D > 20 ≧ C > 4 ≧ B > 0.8 ≧ A | |
|---|---|
| Examples | α 4 β 7 |
| 1 | D |
| 2 | A |
| 3 | B |
| 5 | A |
| 6 | D |
| 7 | D |

It is thus apparent that the new phenylpropionic acid derivatives exhibited an excellent α 4-integrin inhibiting activity.

Since the new phenylpropionic acid derivatives of the present invention have excellent α 4-integrin inhibiting activity, the present invention provides a therapeutic agent or preventive agent for diseases in which α 4 integrin-depending adhesion process participates in the pathology, such as inflammatory diseases, rheumatoid arthritis, inflammatory bowel diseases, systemic lupus erythematosus, multiple sclerosis, Sjögren's syndrome, asthma, psoriasis, allergy, diabetes, cardiovascular diseases, arterial sclerosis, restenosis, tumor proliferation, tumor metastasis and transplantation rejection. The above-described inflammatory bowel diseases include Crohn's disease and ulcerative colitis.

The compound of the present invention is effective because it has α 4-integrin inhibiting activity and high stability in plasma.

Further, the compound of the present invention has high bioavailability and/or blood level when administered orally. Therefore, an oral administration of a drug is effective.

What is claimed is:

1. A phenylpropionic acid derivative of the following general formula (1) or pharmaceutically acceptable salts thereof:

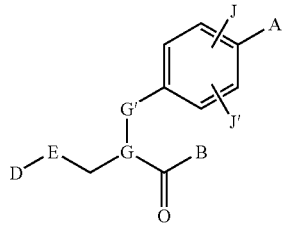

(1)

wherein A represents one of the following general formulae (2-1) to (2-6), —NR1-Z, —NR1-C(=O)-Z, —NR1-SO$_2$-Z, —NR1-C(=O)—NH-Z and —NR1-C(=S)—NH-Z, wherein R1 represents a hydrogen atom, a lower alkyl group, a lower alkenyl group, a lower alkynyl group, a lower alkyl group substituted with a cycloalkyl group(s) which may contain a hetero atom(s) in the ring thereof, a lower alkyl group substituted with an aryl group(s) or a lower alkyl group substituted with a heteroaryl group(s), R1 and Z may be bonded together to form a ring which may contain one or two oxygen, nitrogen or sulfur atoms, Z represents the following general formula (2), a lower alkyl group, a lower alkenyl group, a lower alkynyl group, a cycloalkyl group which may contain a hetero atom(s) in the ring thereof, an aryl group, a heteroaryl group, a lower alkyl group substituted with a cycloalkyl group(s) which may contain a hetero atom(s) in the ring thereof, a lower alkyl group substituted with the general formula (2), a lower alkyl group substituted with an aryl group(s), a lower alkyl group substituted with a heteroaryl group(s), a lower alkenyl group substituted with a cycloalkyl group(s) which may contain a hetero atom(s) in the ring thereof, a lower alkenyl group substituted with an aryl group(s), a lower alkenyl group substituted with a heteroaryl group(s), a lower alkynyl group substituted with a cycloalkyl group(s) which may contain a hetero atom(s) in the ring thereof, a lower alkynyl group substituted with an aryl group(s) or a lower alkynyl group substituted with a heteroaryl group(s),

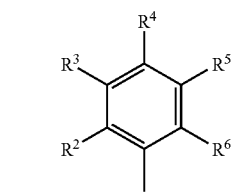

(2)

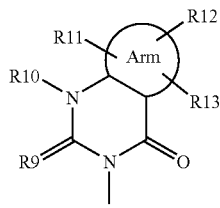

(2-1)

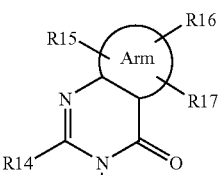

(2-2)

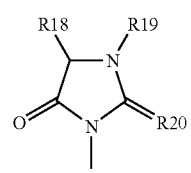

(2-3)

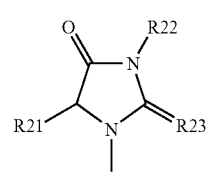

(2-4)

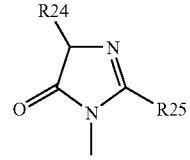

(2-5)

wherein R2 to R6, R10 to R17, R21, R22 and R24 to R28 may be the same or different from one another and each represent a hydrogen atom, a halogen atom, a hydroxyl group, a lower alkyl group, a lower alkenyl group, a lower alkynyl group, a cycloalkyl group which may contain a hetero atom(s) in the ring thereof, an aryl group, a heteroaryl group, a lower alkyl group substituted with a cycloalkyl group(s) which may contain a hetero atom(s) in the ring thereof, a lower alkyl group substituted with an aryl group(s), a lower alkyl group substituted with a heteroaryl group(s), a lower alkoxyl group, a lower alkoxyl group substituted with a cycloalkyl group(s) which may contain a hetero atom(s) in the ring thereof, a lower alkoxyl group substituted with an aryl group(s), a lower alkoxyl group substituted with a heteroaryl group(s), a cycloalkyloxy group which may contain a hetero atom(s) in the ring thereof, an aryloxy group, a heteroaryloxy group, a lower hydroxyalkyl group, a lower hydroxyalkenyl group, a lower hydroxylalkoxyl group, a lower halogenoalkyl group, a lower halogeno alkoxyl group, a lower halogenoalkenyl group, nitro group, cyano group, a substituted or unsubstituted amino group, carboxyl group, a lower alkyloxycarbonyl group, a substituted or unsubstituted carbamoyl group, a lower alkanoyl group, an aroyl group, a lower alkylthio group, a lower alkylsulfonyl group or a substituted or unsubstituted sulfamoyl group, Arm represents a benzene ring, a cyclic alkyl group or an aromatic ring containing 0, 1, 2, 3 or 4 hetero atoms selected from the group consisting of oxygen, sulfur and nitrogen atoms, R9, R20 and R23 may be the same or different from one another and each represent an oxygen atom, a substituted or unsubstituted imino group or a sulfur atom, R18 and R19 may be the same or different from one another and each represent a hydrogen atom, a lower alkyl group, a lower alkenyl group, a lower alkynyl group, a cycloalkyl group which may contain a hetero atom(s) in the ring thereof, an aryl group, a heteroaryl group, a lower alkyl group substituted with a cycloalkyl group(s) which may contain a hetero atom(s) in the ring thereof, a lower alkyl group substituted with an aryl group(s), a lower alkyl group substituted with a heteroaryl group(s), a lower alkenyl group substituted with a cycloalkyl group(s) which may contain a hetero atom(s) in the ring thereof, a lower alkenyl group substituted with an aryl group(s), a lower alkenyl group substituted with a heteroaryl group(s), a lower alkynyl group substituted with a cycloalkyl group(s) which may contain a hetero atom(s) in the ring thereof, a lower alkynyl group substituted with an aryl group(s), a lower alkynyl group substituted with a heteroaryl group(s), a lower halogenoalkyl group, a lower halogenoalkenyl group, a lower hydroxyalkyl group, a lower hydroxyalkenyl group, or a substituted or unsubstituted lower aminoalkyl group, and R18 and R19 may be bonded together to form a ring which may contain one or two oxygen, nitrogen or sulfur atoms, a substituent(s) thereof is a hydrogen atom, a halogen atom, a hydroxyl group, a lower alkyl group, a lower alkenyl group, a lower alkynyl group, a cycloalkyl group which may contain a hetero atom(s) in the ring thereof, an aryl group, a heteroaryl group, a lower alkyl group substituted with a cycloalkyl group(s) which may contain a hetero atom(s) in the ring thereof, a lower alkyl group substituted with an aryl group(s), a lower alkyl group substituted with a heteroaryl group(s), a lower alkanoyl group, an aroyl group, a lower halogenoalkanoyl group, a lower alkyloxy group, nitro group, cyano group, a substituted or unsubstituted amino group, carboxyl group, a lower alkoxyl carbonyl group, a substituted or unsubstituted carbamoyl group, a lower alkylthio group, a lower alkylsulfonyl group or a substituted or unsubstituted sulfamoyl group, B represents a hydroxyl group, a lower alkoxyl group, hydroxylamino group, amino group or a lower alkylamino group, D represents a lower alkyl group, a cycloalkyl group(s) which may contain a hetero atom(s) in the ring thereof, an aryl group or a heteroaryl group, and each may have a substituent(s), E represents C=O or CHOH, G–G' represents CH—CH2 or C=CH, and J and J' may be same or different from one another and each represent a hydrogen atom, a halogen atom, a lower alkyl group, a lower alkyloxy group or nitro group.

2. The phenylpropionic acid derivatives or pharmaceutically acceptable salts thereof according to claim 1, wherein A represents either one of the general formulae (2-1) to (2-6), —NR1-Z, —NR1-C(=O)-Z and —NR1-SO$_2$-Z, Z represents the general formula (2), a lower alkyl group, a lower alkenyl group, a lower alkynyl group, a cycloalkyl group which may contain a hetero atom(s) in the ring thereof, an aryl group, a heteroaryl group, a lower alkyl group substituted with a cycloalkyl group(s) which may contain a hetero atom(s) in the ring thereof, a lower alkyl group substituted with the general formula (2), a lower alkyl group substituted with an aryl group(s) or a lower alkyl group substituted with a heteroaryl group(s), B represents a hydroxyl group or a lower alkoxyl group, and D represents a lower alkyl group, a cycloalkyl group(s) which may contain a hetero atom(s) in the ring thereof, an aryl group or a heteroaryl group, and each may have a substituent(s).

3. The phenylpropionic acid derivatives or pharmaceutically acceptable salts thereof according to claim 1, wherein E represents C=O and G–G' represents CH—CH2.

4. The phenylpropionic acid derivatives or pharmaceutically acceptable salts thereof according to claim 2, wherein each of J and J' is a hydrogen atom.

5. The phenylpropionic acid derivatives or pharmaceutically acceptable salts thereof according to claim 4, wherein A represents either one of the general formulae (2-1) to (2-6).

6. The phenylpropionic acid derivatives or pharmaceutically acceptable salts thereof according to claim 4, wherein A represents —NR1-C(=O)-Z.

7. The phenylpropionic acid derivatives or pharmaceutically acceptable salts thereof according to claim 1, wherein A represents either one of the general formulae (2-1) to (2-6), —NR1-Z, —NR1-C(=O)-Z and —NR1-SO$_2$-Z, Z represents the general formula (2), a lower alkyl group, a lower alkenyl group, a lower alkynyl group, a cycloalkyl group which may contain a hetero atom(s) in the ring thereof, an aryl group, a heteroaryl group, a lower alkyl group substituted with a cycloalkyl group(s) which may contain a hetero atom(s) in the ring thereof, a lower alkyl group substituted with the general formula (2), a lower alkyl group substituted with an aryl group(s) or a lower alkyl group substituted with a heteroaryl group(s), B represents a hydroxyl group or a lower alkoxyl group, E represents C=O, G–G' represents CH—CH2, each of J and J' is a hydrogen atom, and D represents an aryl group or a heteroaryl group, and each may have a substituent(s).

8. The phenylpropionic acid derivatives or pharmaceutically acceptable salts thereof according to claim 7, wherein A represents either one of the formulae (2-1) to (2-6).

9. The phenylpropionic acid derivatives or pharmaceutically acceptable salts thereof according to claim 7, wherein A represents —NR1-C(=O)-Z, Z represents the general formula (2) wherein R2, R3, R4, R5 and R6 may be the same or different from one another and each represent a hydrogen atom or a halogen atom, a cycloalkyl group which may contain a hetero atom(s) in the ring thereof or a heteroaryl group.

10. The phenylpropionic acid derivatives or pharmaceutically acceptable salts thereof according to claim 8, wherein A represents the formula (2-1).

11. The phenylpropionic acid derivatives or pharmaceutically acceptable salts thereof according to claim 8, wherein D represents an aryl group or a heteroaryl group which may have a substituent(s).

12. The phenylpropionic acid derivatives or pharmaceutically acceptable salts thereof according to claim 10, wherein D represents an aryl group or a heteroaryl group which may have a substituent(s).

13. The phenylpropionic acid derivatives or pharmaceutically acceptable salts thereof according to claim 12, wherein D represents a phenyl group or pyridyl group having the substituents on the second position and the sixth position thereof and the substituents thereof are a halogen atom or a lower alkyl group.

14. The phenylpropionic acid derivatives or pharmaceutically acceptable salts thereof according to claim 1, wherein A represents the formula (2-1), Arm represents a benzene ring, R9 represents an oxygen atom, R10 represents a lower alkyl group, and R11 to R13 represent a hydrogen atom, a halogen atom, a substituted or unsubstituted amino group, nitro group, a lower alkyl group, a lower alkenyl group, a hydroxyl group or a lower alkoxyl group.

15. The phenylpropionic acid derivatives or pharmaceutically acceptable salts thereof according to claim 7, wherein A represents the formula (2-1), Arm represents a benzene ring, R9 represents an oxygen atom, R10 represents a lower alkyl group, and R11 to R13 represent a hydrogen atom, a halogen atom, a substituted or unsubstituted amino group, nitro group, a lower alkyl group, a lower alkenyl group, a hydroxyl group or a lower alkoxyl group.

16. The phenylpropionic acid derivatives or pharmaceutically acceptable salts thereof according to claim 13, wherein A represents the formula (2-1), Arm represents a benzene ring, R9 represents an oxygen atom, R10 represents a lower alkyl group, and R11 to R13 represent a hydrogen atom, a halogen atom, a substituted or unsubstituted amino group, nitro group, a lower alkyl group, a lower alkenyl group, a hydroxyl group or a lower alkoxyl group.

17. A pharmaceutical composition containing a phenylpropionic acid derivative or a pharmaceutically acceptable salt thereof according to claim 1 as an active ingredient.

18. A pharmaceutical composition containing a phenylpropionic acid derivative or a pharmaceutically acceptable salt thereof according to claim 7 as an active ingredient.

19. An α 4 integrin antagonist containing a phenylpropionic acid derivative or a pharmaceutically acceptable salt thereof according to claim 1 as an active ingredient.

20. An α 4 integrin antagonist containing a phenylpropionic acid derivative or a pharmaceutically acceptable salt thereof according to claim 7 as an active ingredient.

21. A therapeutic agent or preventive agent for inflammatory diseases in which α 4 integrin-depending adhesion process participates in the pathology, which contains a phenylpropionic acid derivative or a pharmaceutically acceptable salt thereof according to claim 1 as an active ingredient.

22. A therapeutic agent or preventive agent for inflammatory diseases in which α 4 integrin-depending adhesion process participates in the pathology, which contains a phenylpropionic acid derivative or a pharmaceutically acceptable salt thereof according to claim 7 as an active ingredient.

23. A therapeutic agent or preventive agent for rheumatoid arthritis, inflammatory bowel diseases, systemic-lupus erythematosus, multiple sclerosis, Sjögren's syndrome, asthma, psoriasis, allergy, diabetes, cardiovascular diseases, arterial sclerosis, restenosis, tumor proliferation, tumor metastasis and transplantation rejection, which contains a phenylpropionic acid derivative or a pharmaceutically acceptable salt thereof according to claim 1 as an active ingredient.

24. A therapeutic agent or preventive agent for rheumatoid arthritis, inflammatory bowel diseases, systemic lupus erythematosus, multiple sclerosis, Sjögren's syndrome, asthma, psoriasis, allergy, diabetes, cardiovascular diseases, arterial sclerosis, restenosis, tumor proliferation, tumor metastasis and transplantation rejection, which contains a phenylpropionic acid derivative or a pharmaceutically acceptable salt thereof according to claim 7 as an active ingredient.

* * * * *